United States Patent
Selker et al.

(10) Patent No.: US 7,263,871 B2
(45) Date of Patent: Sep. 4, 2007

(54) SYSTEM AND METHOD FOR GAS ANALYSIS USING DOUBLY RESONANT PHOTOACOUSTIC SPECTROSCOPY

(75) Inventors: Mark Selker, Mountain View, CA (US); Alfred Riddle, Milpitas, CA (US); Barbara Paldus, Woodside, CA (US)

(73) Assignee: Finesse Solutions LLC., Santa Clara, CA (US)

( * ) Notice: Subject to any disclaimer, the term of this patent is extended or adjusted under 35 U.S.C. 154(b) by 124 days.

(21) Appl. No.: 11/245,748

(22) Filed: Oct. 7, 2005

(65) Prior Publication Data
US 2006/0123884 A1    Jun. 15, 2006

Related U.S. Application Data

(60) Provisional application No. 60/688,595, filed on Jun. 7, 2005, provisional application No. 60/634,627, filed on Dec. 9, 2004.

(51) Int. Cl.
*G01N 21/00* (2006.01)
(52) U.S. Cl. .................................... 73/24.02; 73/24.06
(58) Field of Classification Search ............... 73/24.01, 73/24.02, 24.06
See application file for complete search history.

(56) References Cited

U.S. PATENT DOCUMENTS

| | | | |
|---|---|---|---|
| 4,457,162 A * | 7/1984 | Rush et al. | 73/24.01 |
| 5,815,277 A * | 9/1998 | Zare et al. | 356/437 |
| 6,975,402 B2 * | 12/2005 | Bisson et al. | 356/432 |

* cited by examiner

*Primary Examiner*—Daniel S. Larkin
(74) *Attorney, Agent, or Firm*—Herbert Burkard, Esq.

(57) ABSTRACT

A method for analyzing gas concentration using doubly resonant photoacoustic spectroscopy, and a doubly resonant photoacoustic gas detector comprising:
i) a continuous wave light beam whose wavelength coincides with an absorption wavelength of a gaseous analyte;
ii) a closed path optical cavity having at least two reflective surfaces;
iii) an acoustic resonator chamber contained within said optical cavity, and comprising an acoustic sensor for detecting sound waves generated by a gaseous analyte present within said chamber, the light beam passing sequentially into, through and out of said chamber, and being repeatedly reflected back and forth through said chamber, and being modulated at a frequency which is equal to or equal to one-half of an acoustic resonance frequency of said acoustic resonator chamber.

30 Claims, 12 Drawing Sheets

SYSTEM AND METHOD FOR GAS ANALYSIS USING DOUBLY RESONANT PHOTOACOUSTIC SPECTROSCOPY

RELATED APPLICATIONS

This application claims the benefit of co-pending, commonly assigned U.S. Provisional Applications Ser. No. 60/634,627, filed 9, Dec., 2004 and 60/688,595, filed 7 Jun. 2005 the disclosures of which are hereby incorporated in their entirety.

FIELD OF THE INVENTION

The present invention relates generally to the field of gas detection and contaminant concentration analysis. In a preferred embodiment, the present invention relates to (but is not limited to) moisture content monitors.

BACKGROUND OF THE INVENTION

As semiconductor technology advances and device sizes shrink, the impact of contaminants in the gases used to fabricate these devices becomes increasingly important. Many specialty gases are used in the production of semiconductor devices. For example, a major source of contamination in the chip fabrication process is the presence in process gases of trace amounts e.g., on the order of tens of parts per billion by volume (ppbv) of water. While ultra pure (water and other contaminant free) gases are sometimes available, chemical reactions, phase changes, and other effects often result in the presence of moisture in the gas supply line in a semiconductor fabrication system. These facts make it very attractive to have moisture sensors that are small, efficient, have rapid response times, and are inexpensive enough to be placed in multiple locations in the system. These locations include each line of the gas box and also immediately before the reactor in a semiconductor fabrication system. Currently available sensors do not meet all the aforementioned requirements.

Semiconductor fabs require as many as fifty gases to process a wafer. Table 1 lists some of the gases associated with several different process steps. Contaminants in these gases can diminish yields and degrade chip reliability. One common contaminant is water vapor which may distort manufacturing processes and thereby compromise device performance. Process steps which are vulnerable to moisture contamination include epitaxial growth, sputtering, metal-organic vapor phase epitaxy, thermal etching, gas phase etching of tungsten films, plasma etching of silicon and polysilicon, and chemical vapor deposition of polysilicon, silicon dioxide, silicon nitride, and tungsten. The presence of water can accelerate or retard the chemical reactions which occur during deposition or etching, thereby altering the thickness and/or composition of critical layers. Moisture can create pitting, hazing, and stacking faults; cause resist patterns to fail; induce diodes and junctions to leak; and otherwise degrade the service lifetime of products which pass inspection and reach the marketplace. Purity requirements for process gases will likely become more strict as line widths continue to shrink.

The ambient atmosphere typically contains water vapor concentrations of up to, or even exceeding, approximately 1%. This is at least six orders of magnitude greater than the acceptable limits for process gases. As such, even very small leaks of ambient air into the gas distribution system may introduce significant moisture. Furthermore, even well-dried gas lines may contribute moisture to otherwise high-purity gas. After a gas distribution system is purged with an inert gas, some water molecules can remain in the lines due to strong binding to adsorption sites on metal and oxide surfaces. When polar gases, such as HBr and HCl, enter the lines, they tend to displace water molecules, which enter the gas stream. Additionally, surface oxides within the gas distribution system can interact with corrosive gases to create water molecules by chemical reactions such as the following:

$$Fe_2O_3 + 6HCl \Rightarrow 2FeCl_3 + 3H_2O \qquad (1)$$

Since even dry components within the distribution system can spontaneously create water, it seems clear that the semiconductor industry needs real time, in-line moisture monitors to protect wafer fabrication systems from moisture contamination.

TABLE 1

Process Steps and Associated Gases

| Process Steps | Gases (Inert Gases, Hydrides, and Corrosives) | |
|---|---|---|
| Oxidation | Carriers | Ar, $N_2$ |
| | Reactants | $Cl_2$, $H_2$, HCl, $O_2$ |
| Photolithography | Carriers | Ar, $N_2$, |
| Etching | Plasma or Reactive Ion Etching | Ar, $BCl_3$, $Cl_2$, $CF_2$, $CF_4$, $C_2F_6$, He, $H_2$, $N_2$, $O_2$, $C_2F_8$, $SiF_4$, $SF_6$ |
| | Carriers | Ar, $H_2$, Ne, Xe |
| Diffusion | Carriers | Ar, $H_2$, $N_2$, $O_2$ |
| | Dopant Sources | $AsH_3$, $BCl_3$, $B_2H_6$, $PH_3$ |
| Chemical Vapor Deposition | Oxidation | $CO_2$, $N_2$, $O_2$, $H_2SiCl_2$, $SiH_4$ |
| | Doping | $AsH_3$, $B_2H_6$, , $PH_3$, $SiH_4$ |
| | Nitride | $N_2O$, $SiCl_4$, $NH_3$ |
| | III-V Layers | $AsH_3$, $H_2$, HCl, $H_2S$, $PH_3$ |
| Ion Implantation | | Ar, $AsH_3$, $BCl_3$, $BF_3$, $B_{11}F_3$, $Cl_2$, He, $H_2$, $H_2S$, $N_2$, $PH_3$, $SiH_4$, $P_2F_6$, $SiF_4$ |
| Annealing | | Ar, $H_2$, $N_2$ |
| Metallization | | Ar |
| Bonding | | Ar, $H_2$, $N_2$ |
| Crystal Growth | | Ar, He, $H_2$ |
| Epitaxy | Carriers | Ar, $H_2$, $N_2$ |
| | Silicon Sources | $SiH_4$, $H_2SiCl_2$, $HSiCl_3$, $SiCl_4$ |
| | Dopants | $AsH_3$, $B_2H_6$, $PH_3$ |
| | Etchant | HCl |

Additionally, moisture will react with certain gases, yielding acids which corrode gas handling equipment. For example, aqueous hydrochloric acid attacks iron and other constituents of stainless steel. As corrosion advances, pipes, valves, mass flow meters, mass flow controllers, and other components can fail, causing equipment downtime. Furthermore, corroded pipes release particles which enter the gas stream. Gas-phase nucleation by particles and flaking of particles from gas lines onto wafers can reduce yield. According to one report, the gas distribution system accounts for 68% of all contamination in CMOS processes. Moisture in arsine and phosphine lines may also contaminate the ultra-high-vacuum chambers used for doping wafers. Water molecules in the chamber can make it impossible to draw a sufficiently high vacuum, forcing engineers to shut down the chamber and subject it to an extended bake.

Manufacturers of LED's and VCSELs generally deposit three to five epitaxial layers by organometallic vapor phase epitaxy, using ultra-high-purity anhydrous ammonia as a process gas. Trace oxygen in the epitaxial layers can limit device performance. The photoluminescence of LED's and VCSELs depend strongly on the moisture content of the ammonia used during production. In order to increase the efficiency, the amount of moisture needs to be accurately monitored during production.

Kermarrec and co-workers at ST Microelectronics and Air Liquide have studied the effect of moisture on SiGe devices. In their words, "A direct correlation between moisture impurity in process gases and atomic oxygen present in epitaxial SiGe layers was demonstrated, both qualitatively and quantitatively. The resulting incorporation of oxygen atoms can induce dislocations into the strained layers, which may degrade device performance and, subsequently, reliability." O.Kermarrec et.al., *Solid Slate Techology*, 45(3). Pp.55-60, 2002.

Moisture sensors (monitors) are often referred to as in-line or at-line. Generally, in-line refers to a monitor that is sits in the gas line such that the gas under test passes through the monitor without a need for tapping off the line. The term at-line is generally used for monitors that tap some flow off of the gas line. The flow that is tapped off is generally discarded. Both in-line and at-line monitors for semiconductor industry process gases should advantageously have several characteristics, which are not available with current technologies. The monitor should be sensitive enough to detect moisture in concentrations on the order of 10 ppbv (parts per billion volume) or even lower, be fast enough to react to transient changes in gas flows, compact, and inexpensive enough to be placed at multiple locations in the process train. Since none of the technologies available today can satisfy all of these criteria, it is not surprising that wafer fabs rarely deploy in-line moisture monitors. The present invention satisfies an unmet industry need by providing a system which meets all four requirements (sensitivity, speed, size, and price) and is suitable for both in-line and at-line sensors.

Photoacoustic Spectroscopy (PAS) transforms an optical event into an acoustic event. Gas molecules absorb light at specific, characteristic wavelengths and undergo quantized vibrational or rotational transitions. They gain kinetic energy in the form of heat, and collide with other molecules, creating a pressure wave. Since a pressure wave in a gaseous medium is sound, it can be detected by a microphone. The sensitivity of PAS is determined by the efficiency with which the molecular excitation energy produces a pressure wave and the efficiency with which the pressure wave is converted into an electrical signal.

Alexander Graham Bell discovered the photoacoustic effect in 1881. However, scientific and technological interest in the effect lay dormant for eighty years in the absence of suitable light sources and microphones. In the 1960's, lasers stimulated researchers to explore the photoacoustic effect for spectroscopy. In 1968, Kerr and Atwood detected low concentrations of pollutants in air by using lasers and phase-sensitive, lock-in acoustic detection techniques. (E. L. Kerr, and J. G. Atwood, *"The laser illuminated absorptivity spectrophone: a method for measurement of weak absorptivity in gases at laser wavelengths,"* Applied Optics, No 7, p. 915-921, 1968. Kreuzer detected methane in nitrogen in 1971, using an intensity-modulated He-Ne laser (L.B. Kreuzer, "Ultralow gas concentration infrared absorption spectroscopy," *J. Applied Physics*, Vol. 42, p. 2934-2943, 1971.

In order to further elucidate the photoacoustic effects it is useful to consider the physical steps that result in a photoacoustic signal. The photoacoustic effect in a photoacoustic cell can be divided into four sequential events: 1) absorption of incident optical radiation by a target analyte gas; 2) localized heat release in the sample gas due to transformation of the absorbed light energy into molecular motion; 3) pressure wave generation due to heat induced expansion of the gas; and 4) detection of the pressure wave generated acoustic signal. spectroscopy, and also on optimization of the physical system used to carry out photoacoustic There is a large body of work on both the theoretical fundamentals of photoacoustic spectroscopy, and also on optimization of the physical system used to carry out photoacoustic spectroscopy. Specifically, it is known that the configuration of the cell in which the gas is contained can influence the detection process. The first cells were simple cylinders with windows at each end which were substantially transparent to the optical excitation beam. An advance in sensitivity was made when it was realized that the optical signal entering the cell could be modulated to induce a pressure wave at an acoustic resonance frequency of the cell, thereby providing a forcing function. This pressure wave can be detected using a microphone attached to the wall of the cell. If the cell dimensions are picked randomly and/or the optical excitation beam has a high overlap with more than one acoustic mode, the result is typically the excitation of higher order modes and/or weak signal strength at the detector.

Today several companies sell PAS systems, which typically consist of a laser light source, an acoustic cell, a sonic transducer to convert a pressure pulse to a voltage pulse, and electronics for digitizing and storing the output signal from the transducer. The more sensitive systems employ large, high-power lasers. Prior art photoacoustic systems for detecting water generally use CO or $CO_2$ lasers. These lasers are expensive, bulky, and require external cooling. Therefore, although existing systems generally meet the requirements of scientific users, they are clearly not suited for use in an industrial in-line or at-line gas sensor configuration.

In 1996, a group at the Hungarian Academy of Sciences reported using a photoacoustic cell placed inside the optical cavity of a diode laser to achieve an order of magnitude gain in detection efficiency compared to extracavity operation. (Z. Bozoki, et.al., *Appl Phys.*, B 63, 399 (1966). The same group later described a PAS system which supplied optical power with a DFB laser (M. Szakáll, Z. Bozôki, A. Mohâcsi, A. Varga, and G. Szabô, "Diode Laser Based Photoacoustic Water Vapor Detection System for Atmospheric Research," *Applied Spectroscopy*, Volume 58, Number 7, 792-798, 2004). This system reportedly was able to detect moisture at levels of about 250 ppbv. The system would appear to have come within a factor of about twenty-five of the minimum required sensitivity for semiconductor gases, but did not meet the criteria for industrial use in terms of size or cost. Italian workers (A. Boschetti, et.al., Appl. Phys., B 74, 273-278 (2002), reported use of a pulsed laser for methane and ethylene detection. Additionally, they referred to the earlier Hungarian work and stated "Placing the resonant PA cell inside an external build-up cavity will provide a higher gain while maintaining the possibility of pressure control in the sampling cell." No further details were given so it is unclear what type of laser or detector configuration they were contemplating.

Clearly, methods and systems for increasing the sensitivity of photoacoustic spectroscopy units, while simultaneously reducing their size and the cost are essential if widespread industrial use is to be realized. Widely deployable systems for industrial use will require small and inexpensive light sources, such as the CW diode lasers heretofore developed for telecommunications use. These lasers are small, relatively inexpensive, and convert electrical energy into optical energy with high efficiency.

SUMMARY OF THE INVENTION

The present invention provides a photoacoustic system and method which can use a wide variety of continuous wave (CW) lasers, including inexpensive telecom diode lasers. It provides a small, optically based sensor that is capable of detecting trace contaminants, such as water vapor, at the level of a few ppbv in both inert and corrosive process gases. In-line or at-line monitors according to the present invention will enable wafer fabs to establish correlations between moisture and/or other contaminant gas content and device quality. Precise knowledge of the relationship between contaminant content and device quality will accelerate yield improvement when fabs are introducing new processes. Given the short product lifetime of today's integrated circuits, it is economically vital to bring new circuits to market as soon as possible. When leaks occur in the gas distribution system, moisture monitors in accordance with the present invention will help wafer fab engineers identify the exact location and severity of the leaks sooner and more easily and thereby cut the associated equipment downtime from hours or even days to minutes. In-line or at-line monitors will help engineers identify the root cause of a yield hit sooner, either by revealing a moisture or other contaminant problem or by enabling them to rule out e.g., moisture as the offender. Furthermore, monitors in accordance with the present invention will enable wafer fabs to optimize the frequency of process tool maintenance by using moisture readings to indicate if maintenance is due. By optimizing the frequency of maintenance, wafer fabs will minimize costs associated with test wafers and other consumables. The present invention will also enable wafer fab engineers to measure moisture in process tools after preventive maintenance. After routine preventive maintenance of tools, such as a CVD chamber, engineers normally purge the chamber to remove moisture. However, they typically have no objective measure of when the moisture content has been reduced sufficiently to stop the purge and resume fabrication processes. The monitors of the present invention will enable them to ensure safe moisture levels and to return the tool to productivity as soon as possible.

For in-line or at-line use, cavity materials for the acoustic chamber of the present invention are advantageously selected to be compatible with the various semiconductor fabrication process gases shown in Table I. These include, but are not limited to quartz, alloys of nickel, TEFLON polytetrafluoroethylene and passivated or electropolished stainless steel, such as 316L. The pressure sensor may be a common electret similar to the type found in hearing aids, or any other sensor of comparable sensitivity (e.g.:>1 mV/Pascal) that is suitable for use in conjunction with inert gases. Examples of other types of microphones include but are not limited to piezoelectric microphones and magnetic (balanced armature) microphones. For contamination sensitive applications, especially where corrosive gases are used, the sensor should advantageously be constructed out of inert materials such as those listed above for the acoustic chamber. The sensor should not outgas nor otherwise react with the gas being tested.

A unique aspect of the present invention is that it provides a resonant optical cavity which enhances the optical power used to excite the target analyte contained within a photoacoustic cell. The resonant optical cavity comprises at least two reflecting surfaces. The simplest configuration is a linear cavity with two mirrors (reflecting surfaces). However, the cavity can be composed of any number of mirrors that create a closed path resonant optical cavity. A stable optical cavity can suitably utilize either flat or concave mirrors, or a combination thereof. For simplicity of fabrication, the mirrors will preferably have the same reflectivity and radius of curvature. As an alternative, one of the reflecting surfaces can be a crossed polarizer. At least one optical element in the system will be translatable so as to change the phase of the electromagnetic wave and enable the optical cavity and the modulated laser source to track one another, so that light builds up inside the optical cavity.

The laser source is modulated appropriately in order to employ a technique known as wavelength modulation spectroscopy, which helps increase detection sensitivity. Tracking means that we maintain the optical cavity length as a multiple of $\lambda(t)/2$, where $\lambda(t)$ denotes the wavelength of the modulated laser beam as a function of time, thereby maintaining the cavity in resonance with the incident modulated laser beam. Alternatively, the laser source can be amplitude modulated rather than wavelength modulated, but in this case some of the noise rejection benefits of wavelength modulation may not be realized.

The present invention provides an optically and acoustically (i.e., doubly) resonant photoacoustic spectroscopy system comprising a resonant acoustic cell contained within an external resonant optical cavity. The effective optical power of a CW laser, such as, for example, a telecom diode laser, is increased by the optical resonance facilitated by the optical cavity provided when for example, two mirrors are provided in the proper alignment and length separation so as to form an optically resonant cavity whose beam passes through the acoustic cavity The prior art has never appreciated or utilized a doubly resonant system in accordance with the present invention..

Two schemes exist for tracking (or locking) the laser and cavity together in order to achieve optical resonance:

"electronic" locking which exploits frequency modulated (FM) sidebands to generate an error signal used by a servo-loop, and "optical" locking which exploits optical feedback between a laser and an external optical cavity or etalon..

The locking system can either move one of the cavity mirrors, as is typically used in electronic tracking (locking), or move the cavity input mirror as is typically used in optical locking. The most well-known electronic locking technique is Pound Drever Hall [see for example Ye, J, Ma, L S, Hall, J L, J. Opt. Soc. Am. B, 15, 6 (1998) or Spence T G, Harb C C, Paldus B A, Zare R N, Willke B, Byer R L., Rev. Sci. Instrum., 71, 347 (2000)], where the frequency sidebands generate an error signal to feedback to the laser wavelength or cavity length. Other electronic locking methods include [Fox, R W, Oates, C W, Hollberg, L W, "Stabilizing diode lasers to high finesse cavities", in Cavity-Enhanced Spectroscopies, eds. Van Zee, R D, Looney, J P, Experimental Methods in the Physical Sciences, Vol. 40, Elsevier Science, New York (2002)] a "periodic" locking combined by diode laser current switching, and tracking by dithering the laser current or cavity length [Romanini D, Kachanov A A, Sadeghi N, Stoeckel F, Chem. Phys. Lett., 264, 316 (1997) and Romanini, A. A. Kachanov, and F. Stoeckel, Chem. Phys. Lett., 270, 538 (1997)]. Electronic locking has been demonstrated for both linear and ring optical cavities. Optical locking has been demonstrated using fixed length V-cavities and dithering the position of the input mirror. "Optical" locking of a DFB laser to a single cavity mode produces a strong effect, which narrows the laser emission spectrum (to match the cavity mode linewidth) and significantly enhances both light injection and transmission through the cavity. Detailed descriptions of both the physics and the detailed implementations of this locking scheme have been reported [Morville, J, Chenevier, M, Kachanov, A A, Romanini, D, SPIE Proc., 4485, 236 (2002) and Morville, J, Romanini, D, Chenevier, M, Kachanov, AA, Appl. Opt., 41, 6980 (2002) and Morville, J, Romanini, D, Kachanov, A A, Chenevier, M, Appl. Phys. B, 78, 465 (2004)].

We use the term "doubly resonant photoacoustic spectroscopy" or "DRPAS" to describe the present invention as it indicates the presence of two resonant chambers: an acoustically resonant chamber, and a second optically resonant chamber which encompasses and amplifies the light intensity inside the acoustic chamber. The acoustic waves generated in the gas sample by the excitation are detected and analyzed. DRPAS in accordance with the present invention can be utilized for almost any fluid (i.e., gas or liquid) that is photoacoustically active and whose absorption peak or peaks coincide with the frequency of a light source capable of supplying optical energy In one embodiment, the present invention provides a doubly resonant photoacoustic spectroscopy system for analyzing gas concentrations. The system comprises an acoustic resonator (resonation chamber) that includes a sensor for detecting sound waves, a first entrance port disposed at one end of the acoustic resonator and a second entrance port disposed at the opposite end of the resonation chamber. For example, the system comprises a first mirror positioned outside of the acoustic resonator adjacent to the first entrance port such that a reflective side of said first mirror faces the first entrance port and a second mirror is positioned outside of the acoustic resonator adjacent to the second entrance port such that a reflective side of the second mirror faces the second entrance port. A laser provides an excitation beam which passes through the first mirror, through the acoustic resonator, through the second entrance port and to the second mirror which reflects the beam back through the chamber to the first mirror. The light beam is repeatedly reflected back and forth between the first and second mirrors whereby these two mirrors form the optical cavity within which the optical power builds up. The current and/or temperature of the laser diode are set such that the wavelength of the laser diode is coincident with the absorption feature of the analyte under study. The current and/or temperature of the laser diode are then modulated which results in the wavelength of the laser diode moving back and forth on the analyte absorption features. A control loop links the laser wavelength modulation to means, such as a piezoelectric transducer, for oscillating one mirror (e.g., the second mirror of a linear cavity) at the same frequency as the acoustic resonance frequency. Although the term entrance port has been used to describe the means of ingress and egress to and from the acoustic cavity, it should be recognized that in a preferred embodiment a window of optical glass or other material substantially transparent to the laser light will be present at each end of the acoustic cavity.

The present invention provides a method for analyzing the concentrations of a wide variety of gases using our doubly resonant photoacoustic spectroscopy (DRPAS) technique. The method comprises the steps of containing a gas sample in an acoustic resonator contained within a resonant optical cavity and exciting the gas sample with a beam of excitation light at a selected excitation wavelength of the analyte. The beam of excitation light is reflected back and forth through the gas sample (for example, by a pair of mirrors in a two mirror system) positioned opposite the ends of the acoustic resonator. In order to keep the optical cavity resonant with the laser source, one mirror of the optical cavity is modulated such that the distance between the mirrors, maintains a distance equal to a multiple of half wavelengths (N $\lambda/2$, where N is an integer). Recall that the excitation beam is modulated, such that the wavelength $\lambda$ changes with time ($\lambda = \lambda(t)$). Therefore, the cavity length is also changed over time in order to maintain a resonance condition; i.e., the condition whereby the cavity length is an integer number of half wavelengths of the excitation light.

BRIEF DESCRIPTION OF THE DRAWINGS

Other objects and advantages of the present invention will become apparent upon reading the detailed description of the invention and the appended claims provided below, and upon reference to the drawings, in which:

DETAILED DESCRIPTION OF THE INVENTION

In understanding the present invention, it is helpful to begin with a brief discussion of the behavior of acoustic waves in a closed volume (i.e., resonator). Insight into this behavior is most commonly obtained by solving equations for the motion of acoustic waves ("acoustic wave equations") in the resonator geometry under study. The simplest acoustic resonator geometry is a cylinder. A solution of the wave equation in cylindrical coordinates provides the allowed acoustic energy distributions, or modes, that are supported by a given resonator. The solutions are usually given by indices which indicate the "order" of the solution, and are related to the number of times the field $P_j$ goes to zero as a function of the relevant coordinate. The most general solution of the acoustic wave Equation in this geometry is given by Equation 2:

$$P_j(r, \phi, z, t) = p_j \text{Cos}(m\phi)\text{Cos}\left(\frac{k\pi z}{L}\right)J_m\left(\frac{\alpha_{mn}\pi r}{R}\right)e^{-i\omega t} \quad (2)$$

In the modal solutions described by Equation 2, the indices k, m, and n (shown in FIG. 1) describe the order of the solution while r,ω, and z are the radial, azimuthal, and longitudinal basis vectors respectively of the cylindrical coordinate system. For instance, the mode solution with k=1, m=0, n=0, is often noted as $F_{100}$ and is the first (lowest order) resonant longitudinal mode. In this lowest order longitudinal mode ($F_{100}$) the field nulls occur at zeroes of the wave in the longitudinal axis as given by $$\text{Cos}\left(\frac{1\pi z}{L}\right).$$

Figure 1:
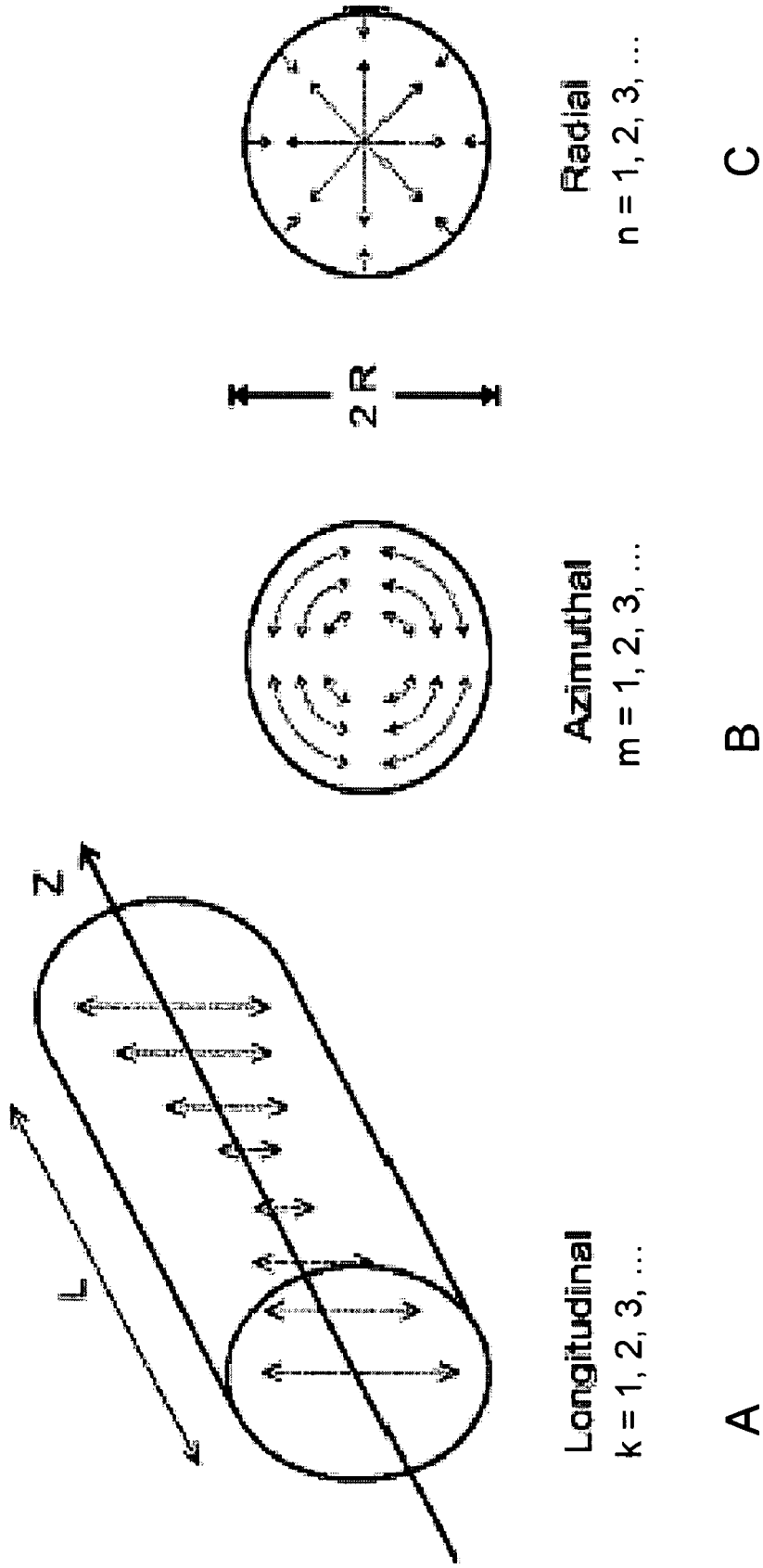
FIGS. 1A-C is a schematic diagram showing the oscillation directions (longitudinal, azimuthal and radial) for the three modes of an acoustic resonator cell. The indices k, m and n as shown are explained below.
Figure 10:
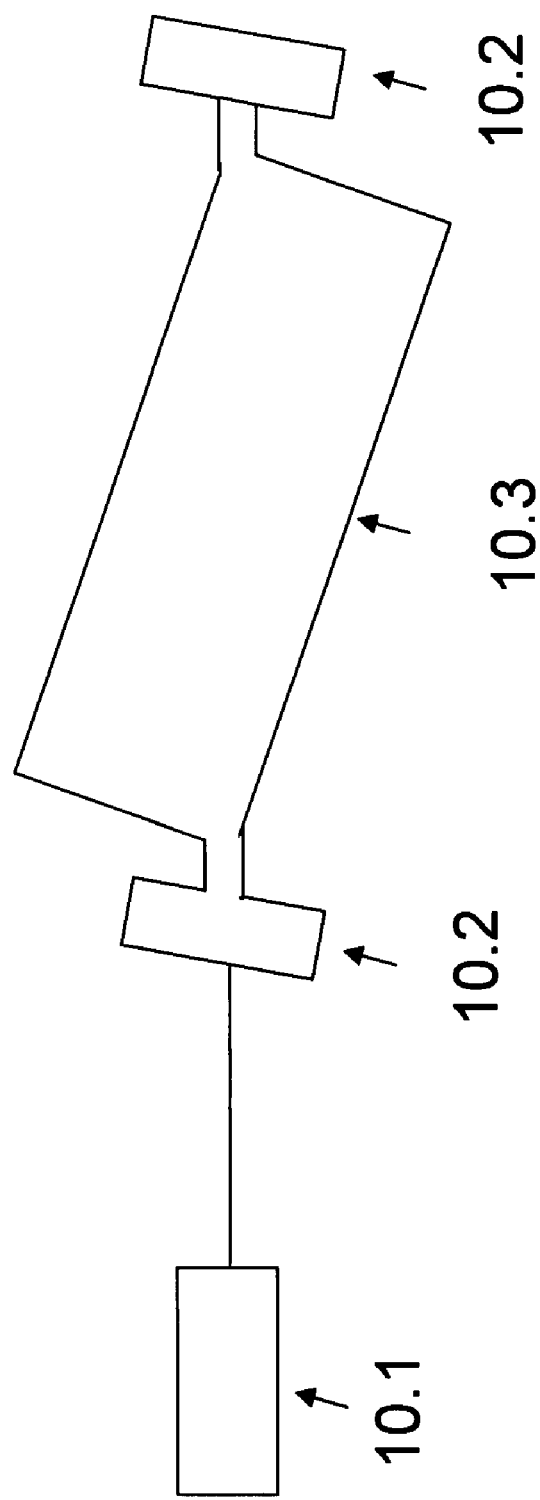
FIG. 10 is a schematic showing one configuration in accordance with the present invention for an acoustic cell used where the fundamental radial mode of the cavity is excited.

Modes referred to as higher order modes have more nulls per unit length along the resonator axis and can also have nulls in the radial and azimuthal field distributions ($P_j$) where $p_j$ is the amplitude of the mode, $\alpha_{mn}$ denotes the zeroes of the radial solution of the wave equation in cylindrical coordinates ($J_m$ are Bessel Functions); R and L are the radius and length of the cylinder, respectively; {k m, n} are mode eigenvalue indices {longitudinal, azimuthal, radial} indicating the order of the mode. The directions of oscillation for these three modes are shown in FIG. 1. Although, we will focus on the longitudinal modes, a closed volume, (i.e., resonator) can oscillate on any one of these modes (longitudinal, azimuthal, or radial). Any solution to [[e]] Equation 2 can be excited at its resonant frequency and thereby produce a photoacoustic signal. If desired, a resonant cell can be constructed that operates by utilizing a radial or azimuthal mode solution. The geometry of the cell will typically reflect which mode is utilized. For example, in the configuration shown in FIG. 10 the fundamental radial mode is excited, so the cell shape and orientation are adjusted to maximize the overlap with the first radial mode. In FIG. 10, 10.1 is the optical excitation source, 10.2 are buffers to reduce noise ingress into the cavity, and 10.3 is the acoustic resonator. Generally, the optical excitation beam is optimized by the use of a suitable optical system (e.g. lenses, mirrors, prisms) to overlap spatially to the maximum extent possible with the mode of interest, and the optical beam is modulated at the resonant frequency of this mode. In order to detect excitation of this mode, it is preferred to place the microphone at the radial or azimuthal mode's pressure maximum in order to gain the maximum benefit from the mode.

Figure 2:
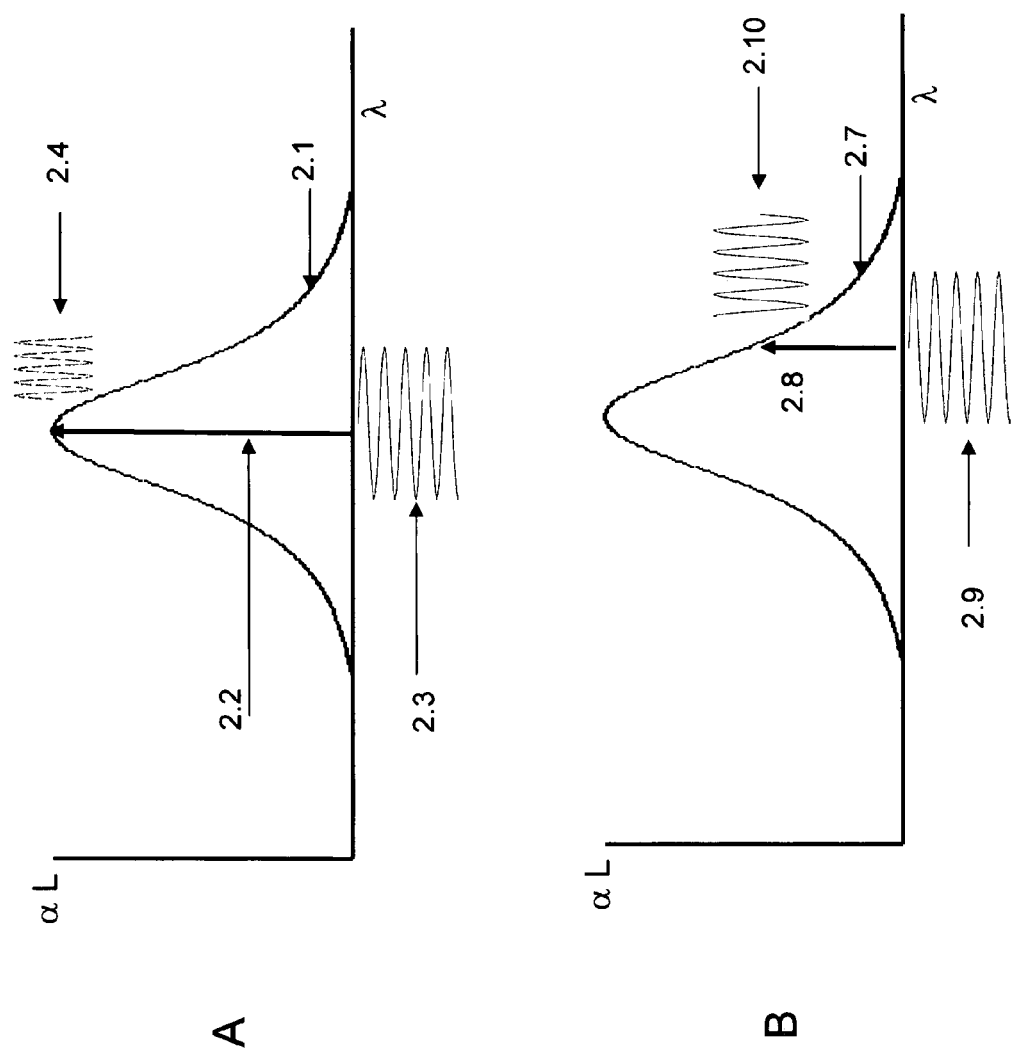
FIGS. 2A-B is a schematic showing the basics of wavelength modulation spectroscopy for 1f and 2f detection.

In order to efficiently excite one of the resonant modes of an acoustic cavity at its resonant frequency, as described by Equation 2, one modulates the absorbed optical power, and thereby the photoacoustically driven pressure in the cell. This can be accomplished by either amplitude or frequency modulating the optical signal. Direct amplitude modulation will cause the direct modulation of the photoacoustic signal, and it will lead to time varying absorbed optical power and hence a time varying photoacoustic signal. It is also possible, and sometimes more advantageous to use frequency modulation; i.e., to modulate the wavelength of the optical excitation source (e.g.: laser). Modulation of the excitation wavelength also leads to a modulation of the photoacoustic signal. One way of accomplishing this is shown in FIG. 2. This is known as wavelength modulation spectroscopy (WMS) and is advantageously employed in conjunction with phase sensitive detection. This combination allows one to detect signals that are produced at multiples of the modulation frequency f. When the laser's wavelength is centered on the absorption feature, only even harmonics are produced, however, if the laser's wavelength is off on one side of the absorption feature, both even and odd signals can be produced. In general, when even harmonics are desired the laser is centered on the peak of the analyte's absorption feature. When the largest signal, the 1f signal, is examined, the laser wavelength is offset from the peak so as to maximize this signal. The corresponding signals resulting from modulation of the laser are thus named 1f, 2f, 3f . . . Nf (N being an integer) signals. It is also true that for very small modulation amplitudes, these Nf signals are proportional to the derivatives of the analyte's absorption feature (lineshape). In many applications, the "2f" signal is particularly useful. The amplitude of this 2f signal is optimized by modulating the laser frequency (shown in FIG. 2A in static position as 2.2, and under modulation as 2.3) such that it travels an amount Δλ in wavelength space equal to 1.1 times the full width at half maximum of the absorption lineshape 2.1 of the analyte under study. The result of the laser's wavelength modulated signal interacting with the absorption of the analyte is a modulated absorbed power 2.4 at twice the frequency of the laser's modulation. One advantage of WMS is the fact that only the target analyte will normally contribute to the signal. This is especially true when detecting the second derivative (2f term). If the 1f term were to be detected. the laser would be centered off of the peak of the absorption feature, as shown in FIG. 2B. The laser is shown in the center of its travel, 2.8, where the first derivative is maximized and under modulation 2.9. The interaction with the absorption feature 2.7 results in a 1f photoacoustic signal 2.10.

The following equation describes the sensitivity of a cylindrical resonant photoacoustic cell operating on the first longitudinal node and indicates the factors to be considered in designing the acoustic cell:

$$S \propto \frac{P\alpha L Q_a}{V\omega} \quad (3)$$

where S is the sensitivity, P is the optical power in the acoustic cavity, α is the absorption coefficient of the target gas, L is the absorption path length, $Q_1a$ is the quality factor of the acoustic cavity, V is the volume of the acoustic cavity, and Ω is the circular frequency. The $Q_a$ of the acoustic cell can be defined as the ratio of the energy stored in the mode to the energy lost during one acoustic cycle. From Equation 3, it can be seen that it is possible to optimize sensitivity (increase S) by increasing the length and decreasing the volume of the acoustic cavity. $Q_a$ can be measured by taking the ratio of the resonant frequency to the width of the resonant feature and represents the enhancement of the acoustic signal's amplitude in the acoustic cavity. Additionally, it should be noted that operating at a lower frequency is advantageous from the perspective of signal strength. Understanding the behavior of resonant acoustic cells makes it possible to optimize their physical characteristics. For instance, it is possible to design a cell such that it operates on a longitudinal mode with an anti-node in the center of the resonator with the acoustic detector being placed at the center. The acoustic resonator length, $L_{res}$ is related to the acoustic wavelength, $\lambda_a$ as follows:

$$L_{res} = n\lambda_a/2 \qquad (4)$$

where n is an integer greater than or equal to one, $L_{res}$ is the acoustic resonator length, and $\lambda_a$ is the acoustic wavelength. A gas detection cell according to the present invention is advantageously designed to maximize the pressure induced. The details of maximizing the pressure, and hence the sensitivity of the detector according to the present invention, are set forth below.

The detection of any target analyte gas in accordance with the present invention is, in fundamental principle, the same for every gas, i.e., provide optical energy at a wave length where the gas molecule absorbs and detect acoustic waves at the appropriate frequency. For the detection of water vapor, it is advantageous to target a strong overtone absorption peak such as, for example, the one found at approximately 1392.53 nm, Resonance at this peak can be achieved using commonly available, relatively inexpensive telecommunications diode lasers. Other strong water absorption peaks can also be used, such as for example the one at 1370.96 nm. Likewise, $CO_2$ at 1.6 microns or $CH_4$ at 1.65 microns are examples of other gasses that can be readily detected using the present invention utilizing lasers that provide optical energy at 1.6 or 1.65 microns, respectively. In addition to DFB diode lasers, other types of CW lasers, such as Fabry Perot type diode lasers, CO, CO2, and lead salt diode lasers are suitable for the practice of the present invention. Particularly preferred for the practice of the present invention are distributed feedback (DFB) lasers, vertical cavity surface emitting lasers (VCSELs), quantum cascade lasers, and fiber lasers. Some fiber lasers and Fabry Perot diode lasers can be locked to an unstabilized cavity through a piezo-electric modulator inside the laser, which adjusts its wavelength. Fiber lasers also bring the benefit of much higher output powers and narrow linewidths to produce very high intracavity powers, and hence very high sensitivity photoacoustic detection. However, in many cases, owing to their compact size and low cost, DFB diode lasers are the preferred laser source for process applications.

The present invention addresses the needs of wafer fabs by creating the first technology (DRPAS) which satisfies all the key requirements for in-line moisture or other trace gas monitors. DRPAS has sufficient sensitivity for this application and is much less expensive than any alternative techniques. It offers fast response time (seconds) and a small footprint (e.g., 12 cm×15 cm×5 cm). Monitors constructed and used according to the various embodiments of the present invention may be incorporated into alarms to warn wafer fab engineers to shut down a gas line, shut down the process tool to which the gas line is leading, and/or diagnose and treat an abnormal situation. Wafer fabs will be able to install these monitors on every line in the gas distribution system and also at the inlet to every process tool. Such in-line/at-line monitors will significantly increase yields and reduce equipment downtime.

The acoustic resonator in a DRPAS according to the present invention is advantageously designed to maximize the pressure response at the microphone. The pressure in the resonator ideally has its maximum at the location of the pressure wave detector. One of skill in the art will readily understand how to optimize the dimensions of the cell based on the teachings provided herein by solving the acoustic wave equations discussed above, with the photoacoustic effect as the forcing function. The cavity may advantageously be designed by proper choice of cavity length and wavelength to have an anti-node (high-pressure area) where the detector is located.

Figure 12:
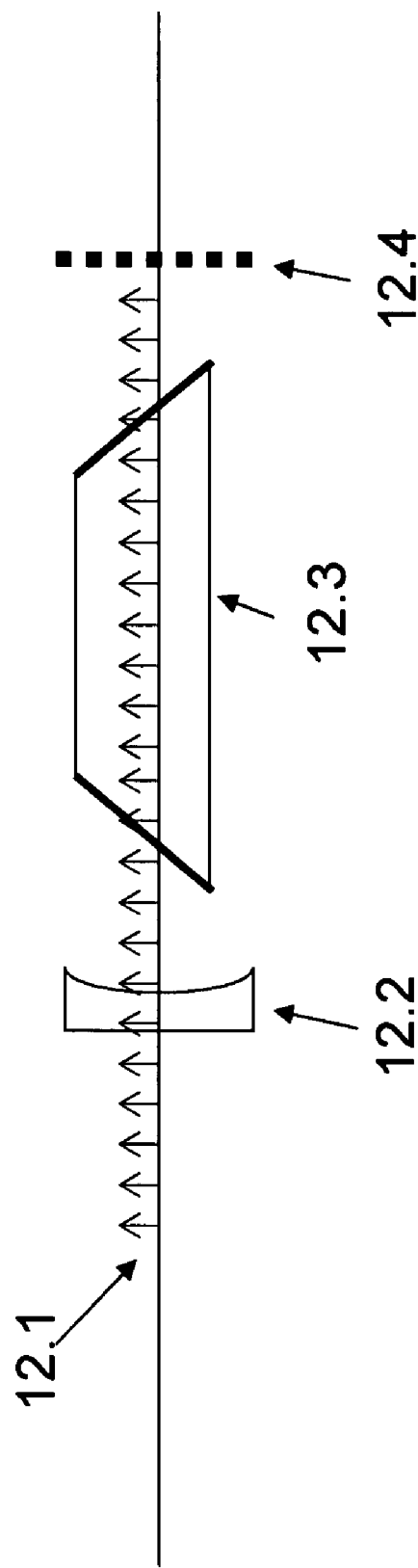
FIG. 12 is a schematic diagram of a resonant optical cavity using a crossed polarizer to replace one end mirror.

Equation 3 shows that detection sensitivity is proportional to L (the acoustic resonator path length) divided by V (the volume). For a cylindrical resonator, L divided by V equals the cross sectional area. Equation 3 indicates that a cylinder with a vanishingly small diameter would have essentially infinite sensitivity. In practice, the minimum practical diameter is limited by turbulence and/or other boundary layer effects near the acoustic resonator's interior walls. Although boundary layer issues impose one practical lower limit on the acoustic cavity's diameter, loss suffered by the Gaussian laser beam as it passes into the acoustic resonator through an aperture ("clipping") can also put a limit on the minimum diameter of the acoustic cell. If the acoustic cell diameter becomes small enough, and the cavity is long enough, the laser beam will clip as it enters and/or exits the cell at each end. The acoustic cell's diameter is advantageously designed to be as small as possible without clipping the laser beam. This minimum diameter depends on the length of the cavity, as well as the wavelength of the excitation beam. Clipping is disadvantageous because it wastes power and can cause heating of the acoustic cavity. The diameter of the optical beam inside the optical resonator is also dependent on the wavelength of the beam as well as the radius of curvature of the mirrors in the optical resonator and also the separation between the mirrors. For a given wavelength, the optical mode diameter is determined by the separation between the mirrors and their radius of curvature so these parameters should be considered when choosing an acoustic resonator diameter. The greater the radius of curvature and separation between the mirrors the larger the mode diameter. It is also possible to utilize a semi-confocal cavity where the planar mirror is replaced with a polarizer. If the light entering and traveling through the system is linearly polarized, a polarizer which is crossed with respect to the light's polarization can serve as a reflector. This is depicted in FIG. 12, where 12.1 is the polarized light entering the optical cavity through a curved mirror 12.2. Part of the light passes through mirror 12.2 with an amplitude depending on the reflectivity of the coating on the inside surface of mirror 12.2. The light then passes through the acoustical resonator 12.3 and impinges upon the polarizer, 12.4, which is crossed, or at ninety degrees with respect to the direction of the polarized light 12.1. The light is then reflected and moves in the opposite direction back towards mirror 12.2. This process continues until the light amplitude reaches steady state in a manner similar to the aforementioned cavities.

Figure 9:
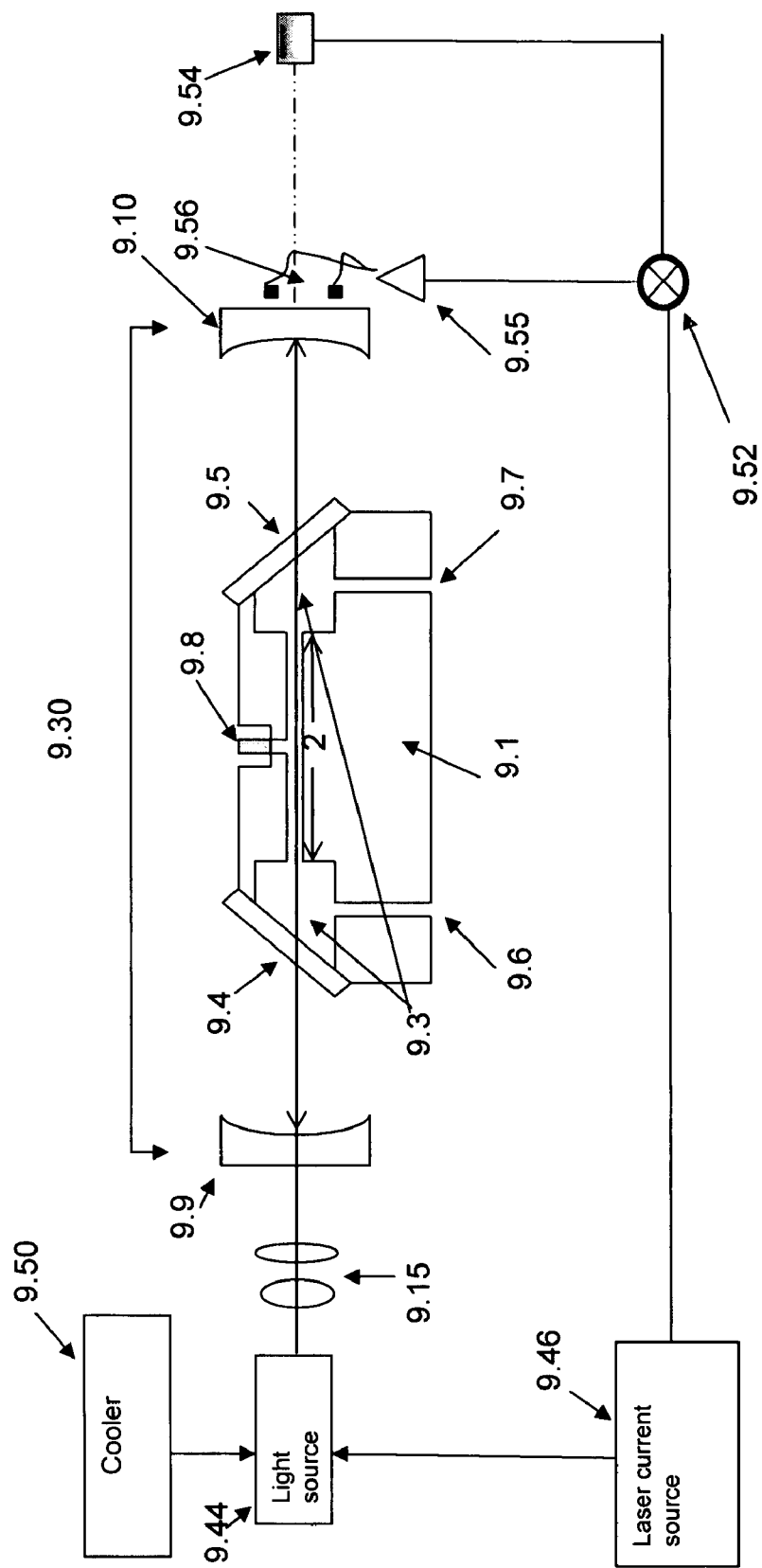
FIG. 9 is a schematic diagram showing a doubly resonant photoacoustic gas sensor according to one embodiment of the present invention.

In the case of a linear acoustic cavity comprised of a central acoustic resonator and two end buffers, the longitudinal acoustic resonance frequency depends on the length of the acoustic resonator. The length of the acoustic resonator will be a multiple of half an acoustic wavelength (i.e., $q=\lambda_a/2$ where q is an integer). The acoustic buffers are generally one quarter wavelength in length. For example, if the acoustic resonance frequency is approximately 8 kHz, this gives an acoustic wavelength of approximately 4 cm in air and a minimum longitudinal acoustic resonant cavity length of 2 cm (i.e., a single half wavelength) with buffers on both sides of the resonator of 1 cm in length each. The entire acoustic cell, would thus be an entire acoustic wavelength long, if quarter wavelength buffers are placed on each side of the acoustic resonator (as shown in FIG. 9) to isolate the system from noise ingress through the windows. For maximum effect, these buffers will suitably have a diameter of at least about four times the diameter of the acoustic resonator itself The resonant frequency may be in the range of from about 1 to about 20 KHz. In a preferred embodiment, the windows of the acoustic cell are mounted at Brewster's angle (Brewster windows) to minimize reflections and therefore loss of the optical beam. Such Brewster windows are known to one skilled in the art.

Figure 3:
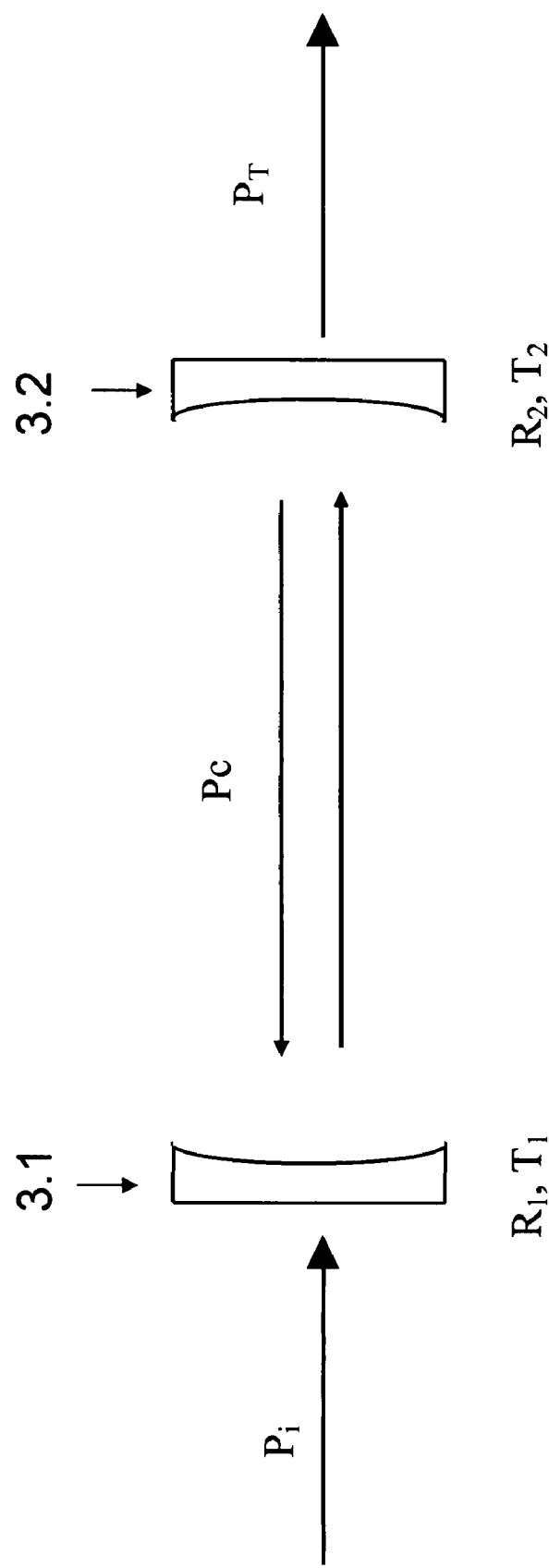
FIG. 3 is a schematic diagram of a two mirror resonant optical cavity in accordance with the present invention.

FIG. 3 is a schematic diagram of a resonant optical cavity in accordance with the present invention. In FIG. 3 $P_i$ is the power incident on mirror 3.1 from outside the optical cavity, $R_1$ and $T_1$ are the reflectivity and transmissivity for mirror 3.1, $R_2$ and $T_2$ are the reflectivity and transmissivity for mirror 3.2 and $P_c$ is the power circulating inside the optical cavity formed by mirrors 3.1 and 3.2. We have found that to a first order approximation one can ignore the optical power loss due to the mirrors since the non-usable mirror losses are negligible. In the concentration regimes of greatest commercial interest (<100 ppmv), the analyte's absorption is also very small. Therefore, the circulating power inside the optical cavity $P_c$ can be expressed as follows:

$$P_c = \frac{T_1 P_i}{\left(1 - \sqrt{R_1 R_2}\right)^2} \quad (5)$$

Equation 5 shows that the circulating power inside the optical cavity ($P_c$) can exceed the incident power density ($P_i$) by several orders of magnitude if a sufficiently high mirror reflectivity is provided. For example, enhancements of between ten and one hundred can be obtained with mirrors which are between 90% and 99.99% reflecting. The enhancement of the optical power within the optical resonator is related to both the finesse of the cavity and also the optical quality factor ($Q_{opt}$). The $Q_{opt}$ of the optical resonator, like the $Q_a$ of the acoustic cavity, may also be defined as the ratio between the energy stored vs. the energy lost during each cycle. It is also is preferable that the linewidth of the laser source be narrower than the linewidth of the resonant optical cavity mode, so that substantially all of the optical source energy can be coupled into the resonant optical cavity.

In general, the sensitivity of a DRPAS system according to the present invention, one embodiment of which is shown in FIG. 9, is directly proportional to the $Q_{opt}$ of the optical cavity. When the acoustic cavity is contained within the optical cavity in accordance with the present invention, the power circulating within the optical cavity becomes the power which determines the sensitivity of the acoustic cavity. In other words, $P_c$ in Equation 5 can be considered as P in Equation 3.

In one embodiment of the present invention, the system comprises an optical cavity with a $Q_{opt}$ of at least twenty-five which can be achieved by selecting mirrors with a reflectivity of at least 90%. If Pc in Equation 5 increases by a factor of ten, hence by Equation 3, the sensitivity of the photoacoustic system also increases by a factor of ten. With no other changes, this optical cavity would improve moisture detectability compared to the prior art e.g., the previously mentioned Hungarian system, from about 250 ppbv to about 25 ppbv.

In order to generate a photoacoustic signal in the analyte, and to optimize the efficiency of 2f wavelength modulation spectroscopy (WMS), the laser is modulated such that the wavelength travels back and forth across the analyte's absorption feature, at about 0.55 times a fullwidth half maximum from the peak on each side of the feature for a total wavelength travel of 1.1 times the full width at half maximum. Additionally, the laser's modulation frequency is one half of the resonance in the acoustic resonator that is to be excited, as the motion across the analyte's absorption feature creates a photoacoustic signal at twice the laser modulation frequency. As mentioned previously, in order to keep the optical cavity resonant with the modulated diode laser frequency, our DRPAS system constantly adjusts the optical cavity length by moving at least one mirror using an appropriate electromechanical device, such as a piezoelectric transducer (PZT). A control loop can execute this task automatically. The control loop can, for example, be a standard derivative type loop. By using phase sensitive detection (e.g. a lock-in amplifier), an error signal can be created that allows one to create a locking loop. As the mirror moves, the location of the cavity transmission peak, moves in frequency space. In the simplest case, we can consider the laser's frequency to be substantially static. In this case, as the cavity mirror is oscillated (i.e., moved back and forth), if the length of the optical cavity is within the appropriate range, this small oscillation in the position of the cavity mirror will sweep the optical cavity transmission peak, across the laser peak. If the laser peak (linewidth) is significantly narrower than the optical cavity's peak the laser will then trace out the transmission feature of the optical cavity. The phase sensitive detector (e.g., a lock-in amplifier) provides an "error signal". The phase sensitive electronics will take the transmission signal and return the first derivative. A peak in the transmission signal will be a null or zero in the first derivative. As the moveable mirror moves far forward, (i.e., closer to the stationary mirror) the derivative signal will be positive/negative; while if this mirror moves backwards, the derivative signal will be negative/positive. The error signal is conditioned (amplified or reduced to the appropriate value) and drives the mirror in such a manner (forward/backwards) in order to reduce the absolute value of the error signal. The feedback loop will always try to maintain a zero error signal. When the error signal is zero, this means that the optical cavity length has been adjusted such that its transmission peak coincides in frequency space with the incident laser source frequency.

Since the acoustic sensor (e.g., a microphone) in a DRPAS system according to the present invention detects changes in acoustic pressure, acoustic disturbances can adversely affect the signal to noise ratio (noise floor). Simulations can be performed to study acoustic noise as a function of the location of the gas inlet and outlet ports of the acoustic cavity. Such simulation results can be used to optimize acoustic filters placed in the gas flow lines and/or baffles near the gas inlet and outlet ports which can serve to reject noise at the frequencies of interest. Acoustic signals can enter the system via the optical windows through heating of the windows or to noise ingress. Buffer regions (i.e., regions of greater diameter) near the windows can advantageously be employed to mitigate the signal created by optical absorption in the window material, and attenuate noise ingress through the windows. For any given system, signal to noise calculations can aid in the decision to detect the pressure signal at the fundamental laser modulation frequency (1f) or at its second harmonic (2f). Detection at the fundamental offers a stronger signal, while detection at the second harmonic generally offers better noise rejection. Detection can also be done at other harmonics if desired.

Figure 4:
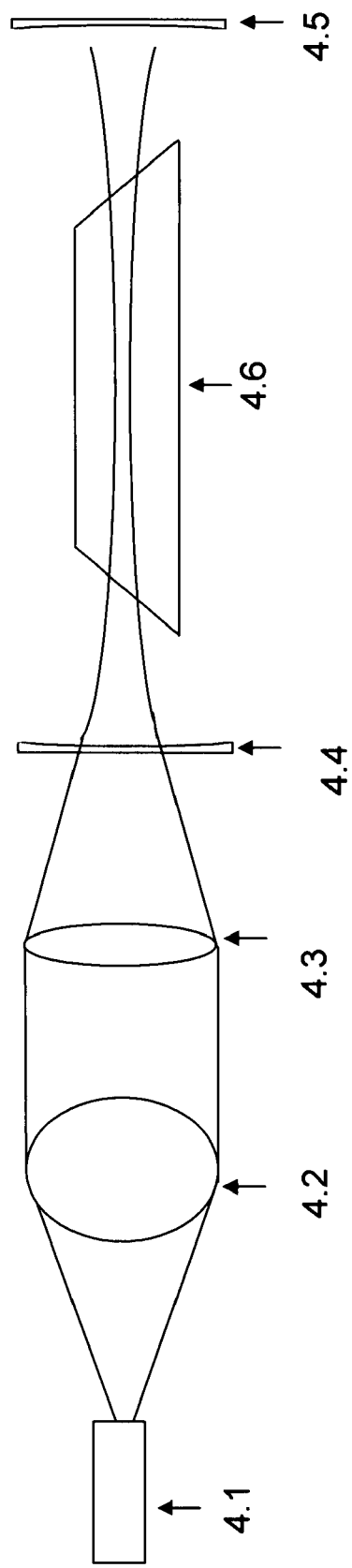
FIG. 4 is a schematic diagram of a lens arrangement suitable for mode matching a Gaussian beam to a resonant optical cavity containing an acoustic resonator in accordance with the present invention.

Specific design parameters of a cavity, which is within the ordinary level of skill in the art based on the teachings of the present invention, includes specifying the mirror reflectivity, the mirror radius of curvature, and the distance between the mirrors. Suitable values for each of these parameters may likewise be established through simulations. The mirror reflectivity determines the power enhancement of the mirror. The radius of curvature together with the mirror separation determines the mode size. Together, the reflectivity, radius of curvature, and separation distance determine the Gaussian width of the cavity mode. An optically resonant cavity is also an optical filter. The higher the reflectivity of the mirrors, the narrower the filter's transmission window. The width of the cavity passband in frequency space is also indicative of the spectral bandwidth of the mode sustained by the cavity. Generally, the narrower the frequency spread of the cavity mode, the more difficult it is to implement a robust feedback loop. This can be understood in terms of tolerances. With a narrow cavity mode and a narrow band laser, it is sometimes difficult to hold the tolerances in positions such that both the optical source and optical cavity always exist at the same frequency. Additionally, the optical resonator formed by the cavity surrounding the acoustic cavity defines an optical mode. In the two mirror embodiments we have described, this mode can be represented by a Gaussian beam as shown in FIG. 4. In FIG. 4, lenses 4.2 and 4.3 are used to collimate and focus the beam emitted by a laser either directly or through an optic fiber 4.1 onto mirror 4.4, which then passes through resonant acoustic cavity 4.6 and is reflected back from mirror 4.5. In order to efficiently couple the laser excitation beam to the mode of the optically resonant cavity, it must have substantially the same spatial profile and phase as the cavity mode at all points in the cavity. This is referred to as mode matching.

Figure 11:
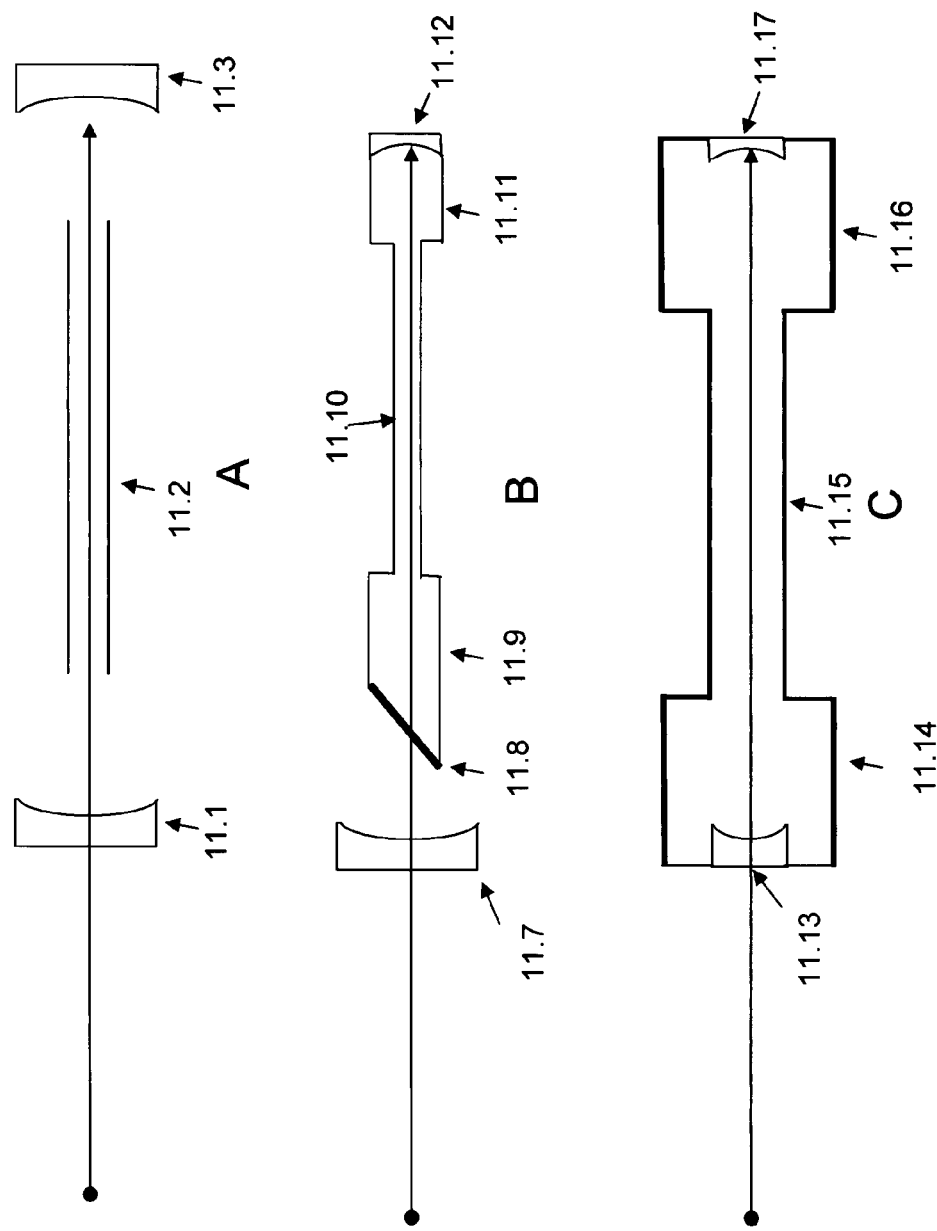
FIG. 11 is a schematic showing alternative designs for the acoustic cell in accordance with the present invention, allowing for constructions with fewer parts.

It is also possible to design acoustic cavities suitable for the practice of the present invention that work with fewer parts. In FIG. 11 three such designs are shown. In FIG. 11 A, 11.1 is the input mirror, 11.2 is the acoustic resonator. In FIG. 11 B, another design is depicted. 11.7 is the input mirror which can oscillate in position along the beam path, 11.8 is shown as a Brewster window, but alternatively could be a wedged or anti-reflection coated flat window, 11.9 is the first buffer, 11.10 is the acoustic resonator 11.11 is the second buffer and 11.12 is the end mirror. The end mirror serves the dual purpose of sealing the cavity and also retro-reflecting the excitation beam. The design shown in FIG. 11C consists of a first end mirror 11.13, a buffer volume 11.14, an acoustic resonator 11.15, a second buffer volume 11.16, and a second mirror 11.17. In FIG. 11C there are no distinct cavity windows as the mirrors serve a dual purpose at each end. It is necessary for at least one of the end mirrors to be mounted, such that it simultaneously can oscillate in position, but still maintain a hermetic seal to the acoustic resonator. The laser light source can be suitably located behind any of the mirrors of FIGS. 11 A-C.

Figure 5:
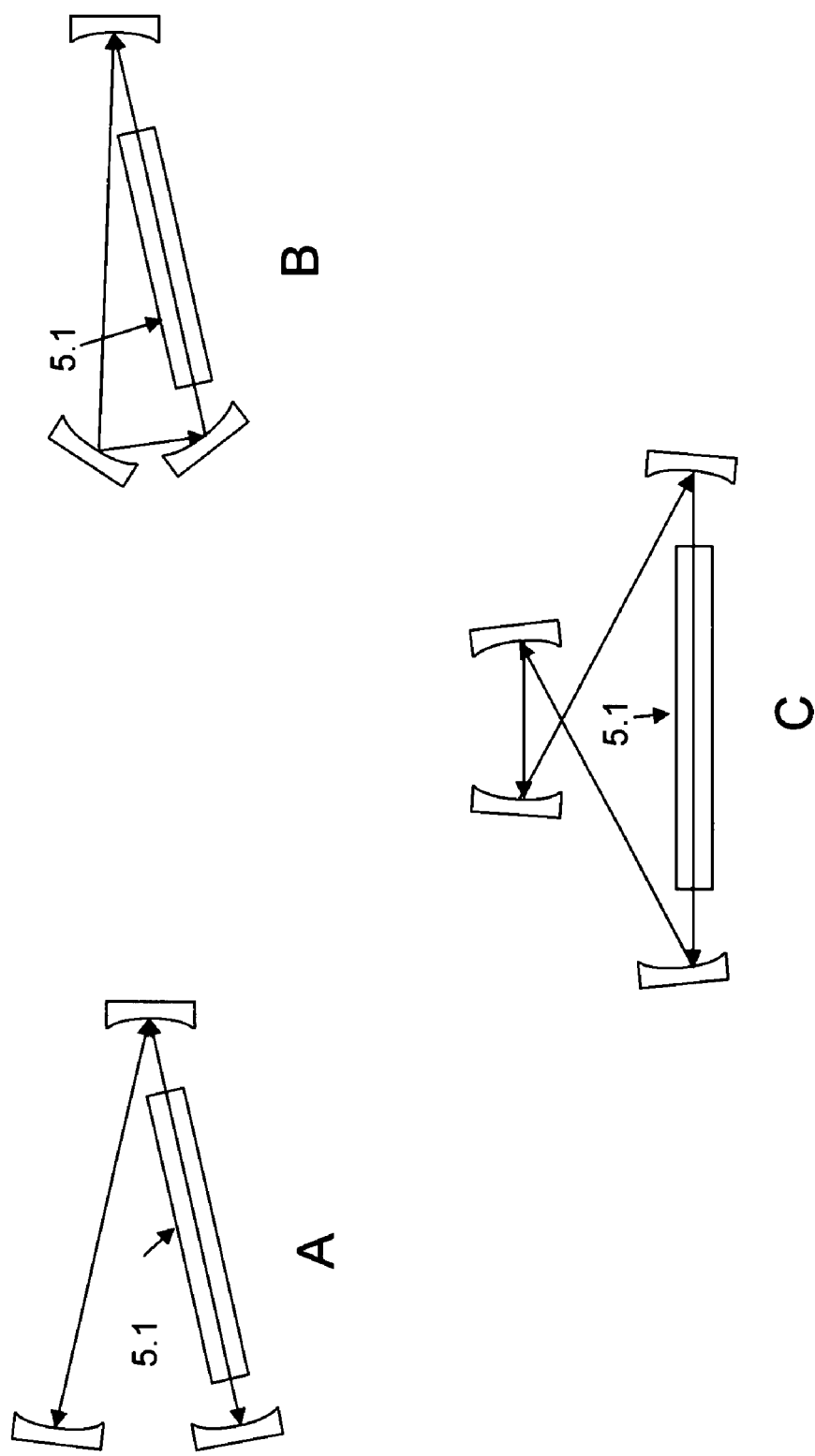
FIGS. 5A-C are schematic diagrams showing several alternative configurations of optical cavities which are suitable for the practice of the present invention.

Although we have described our invention generally in terms of a two mirror optical cavity, it should be obvious to the skilled artworker that three or four mirror cavities (e.g., linear and ring) are also suitable. FIGS. 5A-5C illustrates several alternative configurations of such cavities where 5.1 in each case represents the acoustic cavity and the laser path is shown by the lines between the mirrors indicated as M1 through M4. In FIG. 5, 5A is a three mirror linear cavity, 5B is a three mirror ring cavity, and 5C is a four mirror ring cavity. In general, fewer optical elements are preferred (e.g., a linear two mirror cavity) as there is less optical power loss and a shorter optical path. The free spectral range or spacing of resonance peaks of the cavity is related to the length of the cavity. The longer the cavity, the more closely spaced the resonances. If the analyte's absorption feature is wide compared to the cavity free spectral range, it is possible to have more than one optical cavity transmission peak overlap the analyte's absorption feature. This can make it difficult to lock the optical cavity to the excitation laser.

A system according to the present invention may also include an electronics subsystem that can perform several functions, including but not limited to controlling the laser with bias and modulation current, using a thermoelectric cooler coupled to the laser to set the laser temperature and thereby adjust its emission wavelength, reading the acoustic sensor to determine the response level, outputting an alarm if the response is above a given threshold, setting the modulation frequency depending on the particular target analyte gas, (since the density of each gas is different, the speed of sound is different in each gas, hence the resonant frequency of the acoustic cavity will vary depending on the analyste), controlling the position/oscillation of the optical cavity mirror, reading temperature and pressure sensors, storing data, and communicating with digital electronics via for example, an RS232 communications protocol The digital electronics correlate the acoustic signal with temperature and pressure sensor data to determine the concentration of the target analyte. The system may advantageously use a standard embedded controller for data storage and communication. The control loop may be built from known electronics components, such as lock-in amplifiers, function generators, and diode laser controllers. Phase-sensitive detection of the time-varying acoustic signal enables filtering out of noise, thereby increasing the signal-to-noise ratio. The control loop may use set points from digital memory in a standard feedback configuration As indicated, a system according to the present invention may advantageously use readily available telecom diode lasers which emit, for example, 10 mW of output power at wavelengths, such as approximately 1392.53 nm or 1370.96 nm. These wavelengths correspond to overtones of a strong water absorption feature (peak). The electronic subsystem modulates the laser's drive current so that its wavelength sweeps back and forth across the absorption feature. The period of the laser modulation tracks the resonant frequency of the acoustic cell. For example, the frequency of the laser modulation may be approximately 4 kHz if the first derivative signal is detected or approximately 8 kHz for the second derivative signal The system amplifies and filters the acoustic sensor using phase sensitive detection (e.g.: a lock-in amplifier) technique. To eliminate noise sources which may occur at the fundamental frequency of the resonant acoustic cavity, the detector electronics may be designed to collect data at twice the fundamental frequency. Detecting at a higher frequency has several advantages. The first is that noise typically varies inversely with frequency. This 1/f dependence typically means that there will be less noise when detecting at a higher frequency. Additionally, if the signal is modulated at a frequency f and detected at frequency f, it is more likely that erroneous signals (e.g., background noise and electrical leakage) can enter into the detection path. With 2f detection, this possibility is greatly diminished.

Figure 6:
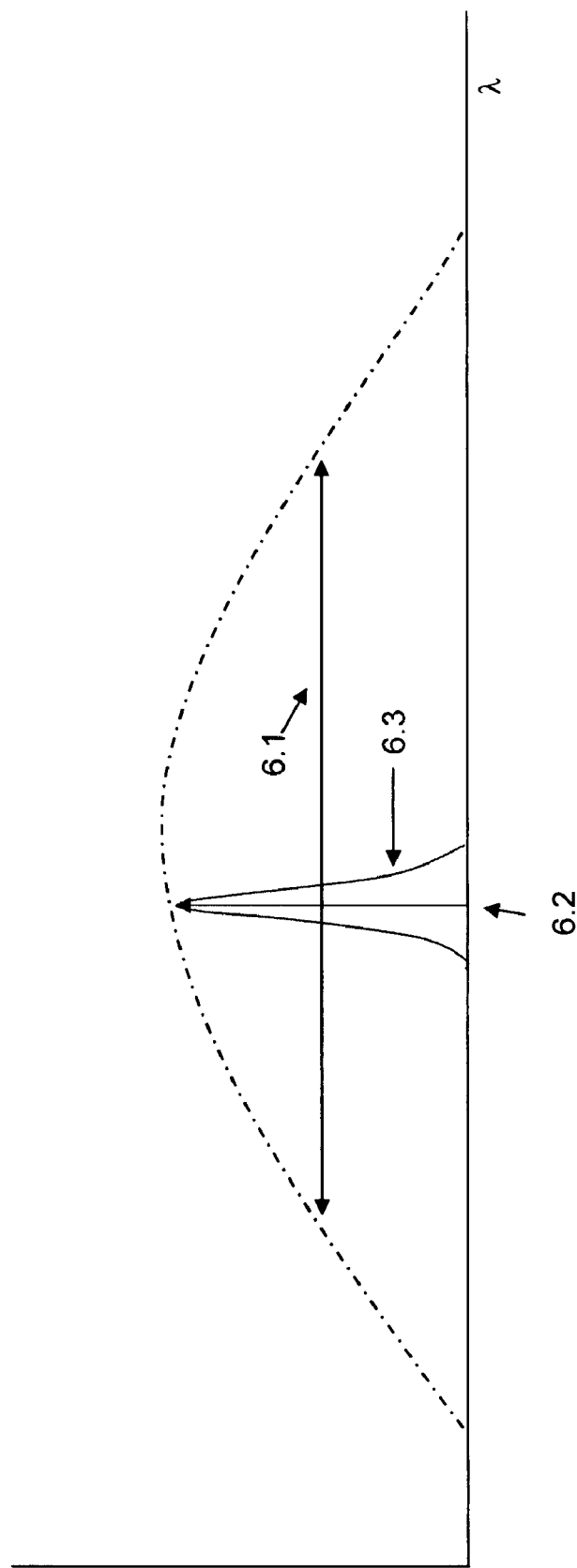
FIG. 6 is a graph showing the relationship between laser wavelength modulation and an example gas absorption feature for a system and method according to one embodiment of the present invention.

As previously indicated, to optimize the power within the optical cavity, the cavity is preferably kept in resonance with the laser, i.e., the cavity length will equal an integral number of half laser wavelengths. The laser wavelength changes continuously as the beam sweeps back and forth across the absorption feature. To maintain resonance, the cavity length changes in synchrony with the laser wavelength modulation. A control loop locks the cavity to the laser; i.e., it adjusts the position of one mirror to keep the cavity and the laser in resonance at a wavelength $\lambda_0$. FIG. 6 illustrates this aspect of the invention when used with 2f detection. The horizontal line 6.1 indicates approximately 1.1 times the full width at half maximum (FWHM) of the absorption feature while the X-axis of the graph represents wavelength. For example, at standard temperature and pressure, the linewidth of water vapor in air is about 6.5 GHz. The line 6.2 represents the laser mode, or laser wavelength. The laser wavelength sweeps back and forth across the absorption feature with a period that equals the resonance frequency $\omega_m$ of the acoustic cell to optimize the pressure signal on the microphone and with an amplitude $\Delta\lambda$ in wavelength space to cover 1.1 FWHM. Line 6.3 represents the resonant optical cavity linewidth. To maximize power in the optical cavity, the laser's power should remain substantially within the cavity linewidth. When the laser wavelength varies, the resonant optical cavity mode will track it.

The challenge of keeping the laser mode within the cavity bandwidth is made easier if the cavity bandwidth is relatively wide, as compared to the laser linewidth. In one embodiment of the present invention, the linewidth of the diode laser is in the range of approximately 0.5 to 1 MHz. The cavity linewidth is in the range of approximately 50 to 100 MHz which is sufficiently broad, considering the linewidth of readily available diode lasers. Keeping the cavity locked to the laser is also easier when the moveable mirror does not have to move a large distance since a piezo electrically driven mirror requires a greater voltage to drive the mirror a greater distance. Additionally, the piezoelectric element itself can act as a capacitor and cause a frequency and amplitude dependent phase shift in the electronics, making the locking loop more difficult to implement. For example, FWHM of the 1392.53 nm line of water is approximately 6.5 GHz wide in frequency space (at STP) which means that the resonant optical cavity mirror has to move its position enough to enable the optical cavity's frequency to change by 1.1 times 6.5 GHz.

Figure 7:
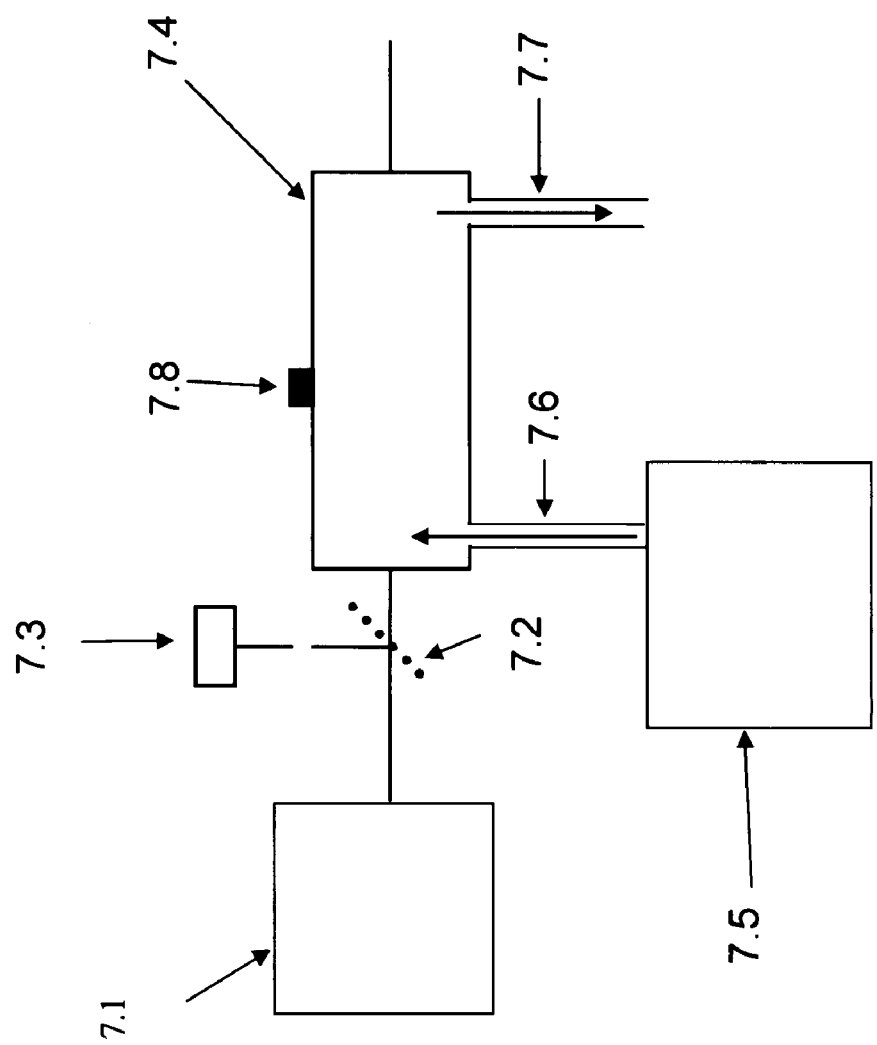
FIG. 7 is a schematic diagram showing test cell and moisture generation reference standard according to one embodiment of the present invention.

The $Q_a$ of the acoustic resonator may be measured with two transducers, one serving as a pressure generator, and the other serving as a pressure detector. The pressure generator is swept through the resonance of the cell, i.e., the pressure generator is operated over a range of frequencies starting below the acoustic cavity resonance frequency and finishing above it. The $Q_a$ equals the ratio of the width of the resonance frequency to the peak frequency. The sensitivity of the acoustic resonator is then tested without the optical resonator being in operation. The baseline data enables quantification of the signal enhancement given by the optical resonator. In order to measure or test the sensitivity of the cell, a NIST traceable moisture generator can be used to produce moisture at a known concentration level as shown in FIG. 7. The moisture generated in a suitable inert gas 7.5 can be flowed through the cell inlet 7.6 into cell (cavity) 7.4 and out the gas outlet 7.7 and the acoustic signal on the detector (e.g., microphone) 7.8 is measured. The laser 7.1 has a small percentage of its power (typically<2%) picked off by a beamsplitter 7.2, and monitored by a photodiode 7.3 which serves as an optical power meter. Given the known concentration of analyte 7.5 under study, measurement of the incident optical power and the acoustic signal give us the sensitivity of our cell.

Figure 8:
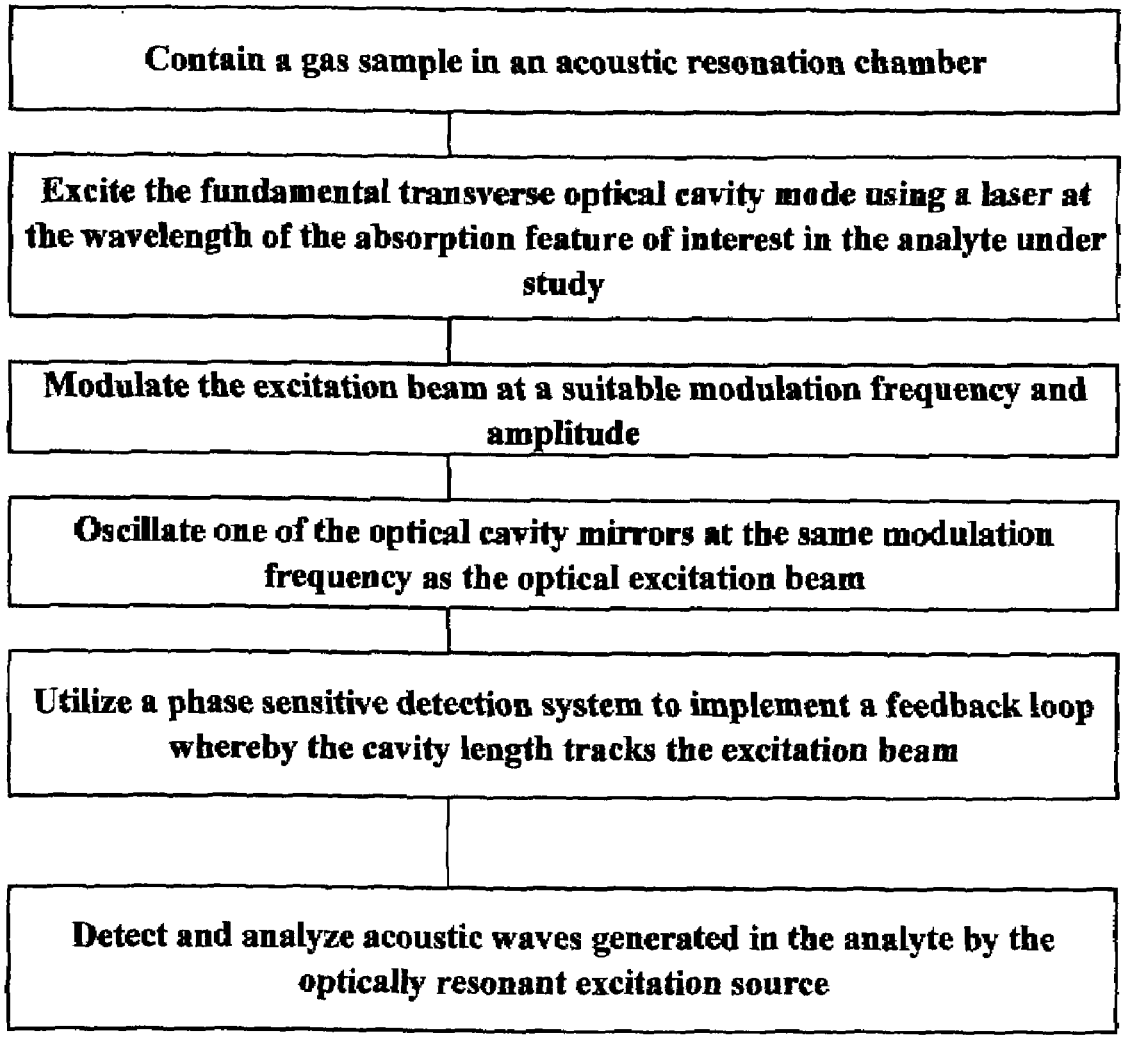
FIG. 8 is a flow chart showing the steps of a gas analysis method according to one embodiment of the present invention.

A detector according to the present invention is particularly suitable to measure moisture in, among other gases, silane, arsine, phosphine, ammonia, and boron hexachloride. Interference-free water absorption lines are readily available against the backgrounds of these hydrides. To detect moisture in hydrides, the acoustic resonant cell may advantageously be lined with TEFLON polytetrafluoroethylene, or fabricated from 316L stainless steel which will preferably be electropolished or otherwise passivated in order to minimize hysteresis caused by the absorption/desorption dynamics of hydrides and water. FIG. 8 is a flow chart illustrating the basic steps of a method for doubly resonant photoacoustic spectroscopy according to one embodiment of the present invention. The first step is to have the analyte under study present in an acoustically resonant cell. This cell will be in the beam path of a resonant optical cavity, typically formed e.g., by two mirrors, as shown. The fundamental ($TEM_{00}$) mode of this cavity is excited by mode matching a light source to this optical cavity. The excitation beam will have a frequency that is close to the peak of the absorption feature of interest in the target analyte. At this time, the excitation beam's wavelength/frequency will be modulated, for example, by directly modulating the current to a diode laser. This modulation will suitably have a frequency that is high enough to avoid low frequency (1/f noise) electronic noise, but low enough that the piezoelectric element driving the motion of the mirror can track it (e.g. $25 \cdot 10^{-2}$ to $10^2$ KHz). For optimized signal 2f detection, the amplitude of the modulation is preferably chosen such that the excitation beam's frequency excursion is equal to $\cong 1.1$ times the full width and half maximum of the analyte's absorption feature. As previously mentioned, one of the cavity mirrors is modulated at the same frequency as the optical excitation beam. The magnitude of the mirror movement is such that the cavity's transmission peak (resonance) moves in frequency space at a rate equal to that of the excitation beam. The feedback loop uses a phase sensitive detection scheme (e.g.: derivative locking or Pound Drever Hall locking (REF) to continuously adjust the phase and the magnitude of the signal to the cavity mirror. By phase sensitive, we mean that if the loop's error signal is either positive, zero, or negative if the cavity transmission peak has a greater frequency, equal frequency, or lower frequency, respectively, than the excitation beam's frequency. Finally, the enhanced acoustic signal generated by the analyte is detected as a pressure wave using a suitable detector as previously described.

Another aspect of sensitivity enhancement according to the present invention is linked to a resonant optical cavity that encircles the acoustic cell, as shown in FIG. 3. The optical cavity is also operated on resonance in that it resonates at the optical frequency of the laser used to excite it. Additionally, the optical cavity has a $Q_{opt}$ which is defined by the ratio of the optical energy stored in the resonator mode divided by the optical energy lost during each cycle. This $Q_{opt}$ defines the optical enhancement of the photoacoustic cell. Since the target analyte gas concentrations of interest are generally very low, the loss caused by the gas itself will normally not have a significant impact on the losses of the cavity; and therefore will not affect the $Q_{opt}$.

The length of the optical cavity is preferably constantly adjusted to maintain it in resonance with the laser diode source, as previously discussed. This length adjustment or locking of the cavity to the laser is accomplished by having at least one cavity mirror mounted on translation means, such as for example, a piezoelectric transducer. A control loop is used to "lock" the cavity to the laser, as has been discussed in greater detail in connection with the embodiment shown in FIG. 8.

FIG. 9 is a schematic diagram of a DRPAS system according to one embodiment of the present invention. In FIG. 9, the system comprises an acoustic cell 9.1, an acoustic resonator 9.2, buffer volumes 9.3, which serve to isolate the resonator from window noise, a first window 9.4 at one end of the acoustic cell, a second window 9.5 at the opposite end of the acoustic cell, near the first window a gas inlet 9.6, near the second window a gas outlet 9.7, and proximate to the center of the acoustic resonator a sensor 9.8, which can be a microphone, transducer or the like. The system further comprises a first mirror 9.9 positioned outside the acoustic cell and opposite the first window 9.4, such that the reflective side of the first mirror faces the first window; and a second mirror 9.10 positioned outside the second window 9.5 with the reflective side of mirror 9.10 facing the second window. The distance between the mirrors 9.9 and 9.10 defines the cavity mode spacing of the optical resonator which is defined by mirrors 9.9 and 9.10. An excitation beam is provided by a laser or other suitable light source 9.44 such that the light beam is mode matched to the optical cavity using suitable optics 9.15, and then passes through the first mirror and into and through the acoustic resonator through the first window. The beam then passes out of the acoustic resonator through the second window before being reflected back into the acoustic resonator by the second mirror. The beam is modulated at half the acoustic resonant frequency of the cavity. When the light source is a laser, the modulation may be provided by adjusting the laser current source 9.46. If another light source is used, such as a filtered bulb or a selected line of a high pressure gas lamp, the modulation can be accomplished with a chopper. Large wavelength changes, if necessary, may be accomplished for a diode laser by a thermoelectric cooler 9.50. Advantageously, a modulated current source 9.46, which provides wavelength modulation, is linked to a lock-in amplifier 9.52. To lock the resonant optical cavity to the laser frequency, a feedback loop is advantageously utilized. In one embodiment, derivative locking can be implemented. This utilizes a lock-in amplifier 9.52, a signal from the cavity provided by, for example, light detected from the cavity by a photodiode 9.54. This signal and the reference signal provided by the modulation source and the laser current driver 9.46 are fed to the lock-in amplifier 9.52 which creates an error signal that is fed to an actuator 9.56 (for example a piezoelectric transducer). The level of the signal is appropriately conditioned by the amplifier 9.55. The actuators move the mirror 9.56 to close the feedback loop.

The foregoing description of specific embodiments and examples of the invention have been presented for the purpose of illustration and description, and although the invention has been illustrated by certain of the preceding examples, it is not to be construed as being limited thereby. They are not intended to be exhaustive or to limit the invention to the precise forms disclosed, and obviously many modifications, embodiments, and variations are possible in light of the above teaching. It is intended that the scope of the invention encompass the generic area as herein disclosed, and by the claims appended hereto and their equivalents.

What is claimed is:

1. A doubly resonant photaoacoustic gas detector comprising:
   i) a continuous wave external light source for generating a light beam whose wavelength coincides with an absorption wavelength of a gaseous analyte;
   ii) a closed path optical cavity having at least two reflective surfaces;
   iii) an acoustic resonator chamber, said acoustic resonator chamber being contained within said optical cavity, and comprising:
   a) an acoustic sensor for detecting sound waves generated by a gaseous analyte present within said chamber,
   b) a first entrance port for admitting light from said external light source into said chamber,
   c) a second port which passes said light out of said chamber after transmission of said light through said first port and said chamber,
   whereby the light beam generated by said external light source passes sequentially into, through and out of said chamber, said light beam being repeatedly reflected back and forth through said chamber, and being modulated at a frequency which is equal to or equal to one-half of an acoustic resonance frequency of said acoustic resonator chamber.

2. The detector of claim 1 wherein said light beam is modulated at a frequency equal to one-half of an acoustic resonance frequency of said acoustic resonator chamber.

3. The detector of claim 2 wherein said closed path optical cavity comprises a first reflective surface facing said first port, and a second reflective surface facing said second port, at least one of said first and second reflective surfaces being translatable.

4. A double resonant photoacoustic gas detector in accordance with claim 2 wherein said first mirror is translated by a piezoelectric transducer.

5. A double resonant photoacoustic gas detector in accordance with claim 2 wherein said first and second windows are Brewster windows.

6. The detector of claim 1 wherein said light beam is modulated at a frequency equal to an acoustic resonance frequency of said acoustic resonator chamber.

7. The detector of claim 1 wherein said closed path optical cavity comprises at least three reflective surfaces, at least one of said at least three reflective surfaces being translatable.

8. The detector of claim 1 wherein the resonance condition of said optical cavity is controlled so as to track the frequency of a wavelength modulatable light beam.

9. The detector of claim 1 wherein the external light source is a laser whose frequency is locked by a second, external optical cavity or etalon.

10. A doubly resonant photoacoustic gas detector in accordance with claim 1 wherein said first and second ports comprise optical windows and wherein said at least two reflective surfaces comprise first and second mirrors separate from, but adjacent to, said first and second windows, respectively.

11. A doubly resonant photoacoustic gas detector in accordance with claim 1 wherein said first and second ports are comprised respectively of first and second reflective surfaces.

12. A doubly resonant photoacoustic gas detector in accordance with claim 1 wherein said first port is a Brewster window, a cross-polarizer or a flat antireflection coated window and sais second port comprises a reflective surface.

13. A doubly resonant photoacoustic gas detector in accordance with claim 1 wherein said first and second ports are windowless.

14. A double resonant photoacoustic gas detector in accordance with claim 1 wherein said optical cavity comprises two mirrors.

15. A double resonant photoacoustic gas detector in accordance with claim 1 wherein said optical cavity comprises three mirrors.

16. A double resonant photoacoustic gas detector in accordance with claim 1 wherein said at least two of said reflective surfaces have a reflectivity of at least 90%.

17. A double resonant photoacoustic gas detector in accordance with claim 1 wherein said acoustic sensor is an electret based microphone, a piezeoelectric based microphone, or a magnetic, balanced armature type microphone.

18. A detector of claim 1 wherein said external light source is a DFB laser, a VCSEL laser, a quantum cascade laser or a fiber laser.

19. A double resonant photoacoustic gas detector in accordance with claim 1 wherein said light source is a diode laser.

20. A double resonant photoacoustic gas detector in accordance with claim 1 wherein said light source is a diode laser emitting light at approximately 1392.53 nm or 1370.96 nm.

21. A double resonant photoacoustic gas detector in accordance with claim 1 wherein said light source is a solid state laser or a $CO_2$ gas laser.

22. A double resonant photoacoustic gas detector in accordance with claim 8 wherein said light source is a fiber laser.

23. A double resonant photoacoustic gas detector in accordance with claim 1 wherein said light source is a quantum cascade laser or an optical parametric oscillator.

24. A double resonant photoacoustic gas detector in accordance with claim 1 wherein said light source and the optical cavity resonant frequency are modulated at substantially the same frequency.

25. A double resonant photoacoustic gas detector in accordance with claim 1 wherein the frequency of said light beam is modulated by translating said translatable reflective surface with a piezoelectric transducer.

26. A double resonant photoacoustic gas detector in accordance with claim 1 wherein said acoustic resonator is substantially cylindrical.

27. A double resonant photoacoustic gas detector in accordance with claim 1 wherein said light source is amplitude modulated.

28. A double resonant photoacoustic gas detector in accordance with claim 1 wherein said sound waves are modulated at a frequency equal to the second harmonic frequency of said light beam.

29. A double resonant photoacoustic gas detector in accordance with claim 1 wherein at least one mirror is replaced by a crossed polarizer.

30. A method for analyzing gas concentration using doubly resonant photoacoustic spectroscopy, comprising the steps of:

containing a gas sample in an acoustic resonator contained within a resonant external optical cavity;

exciting the gas sample with a beam of excitation light having a wavelength where the gas being analyzed has an absorption feature;

said beam of excitation light being reflected back and forth through said gas sample by at least two reflecting surfaces of said resonant external optical cavity;

oscillating at least one of the reflecting surfaces over a distance such that the external optical cavity tracks the excitation beam's full excursion in wavelength space of 1.1 times the full width at half maximum of the absorption feature of said sample gas.

* * * * *